United States Patent [19]

Steele et al.

[11] 4,145,260

[45] Mar. 20, 1979

[54] PROCESS FOR DRYING WATER-WET METHYL CHLORIDE

[75] Inventors: John M. Steele, Lake Jackson; Guillermo J. Nino, Houston; Fredric M. Hanak, Lake Jackson, all of Tex.

[73] Assignee: The Dow Chemical Company, Midland, Mich.

[21] Appl. No.: 486,539

[22] Filed: Jul. 8, 1974

[51] Int. Cl.$^2$ .............................................. B01D 3/36
[52] U.S. Cl. ........................................ 203/14; 203/34; 203/50; 260/654 S; 260/657
[58] Field of Search .................. 203/12, 14, 34, 50; 260/654 S, 657

[56] References Cited

U.S. PATENT DOCUMENTS

| 2,308,170 | 1/1943 | Green et al. | 260/657 |
| 3,499,941 | 3/1970 | Givens et al. | 260/657 |

*Primary Examiner*—Frank Sever
*Attorney, Agent, or Firm*—G. R. Baker; A. C. Ancona

[57] ABSTRACT

A process for recovering substantially dry methyl chloride from a stream of wet methyl chloride by distilling the wet methyl chloride in the presence of at least 10 molar % hydrogen chloride based on the hydrogen chloride, methyl chloride and water being distilled. The distillation is carried out under super atmospheric pressure and a temperature to produce an aqueous hydrochloric acid of less than 36 wt %, and preferably under such super atmospheric pressure and sufficient temperature to produce an azeotropic hydrochloric acid containing a low concentration of hydrogen chloride. Increasing pressures allows increasing temperatures in the bottoms which form azeotropes of lower concentration hydrochloric acid. The resulting overhead of such a distillation, methyl chloride-hydrogen chloride, will contain less than about 400 molar ppm water. When the distillation is carried out in the presence of about 12 to 25 molar % hydrogen chloride, the overhead will contain between about 100 to 400 molar ppm water.

6 Claims, No Drawings

PROCESS FOR DRYING WATER-WET METHYL CHLORIDE

BACKGROUND OF THE INVENTION

The production of methyl chloride ($CH_3Cl$) by the reaction of methanol and hydrogen chloride is well known. However, some difficulty has been encountered in the recovery and purification of the methyl chloride from the reaction mixture. For example, simple distillation of the reaction mixture has resulted in loss of product through reversibility of the reaction under the conditions of the distillation. In addition, the water and methyl chloride form an azeotrope which is difficult to break. To overcome these problems, the art has resorted to sulfuric acid drying of the distilled product, a process which requires large quantities of the sulfuric acid which is either discarded or dried itself and freed of organics prior to reuse.

It would thus be advantageous to have a process for drying which would not favor the reversible reaction and which would result in a useable by-product and not introduce chemicals foreign to the overall system.

BRIEF DESCRIPTION OF THE INVENTION

In accordance with the present invention, methyl chloride is obtained substantially dry (i.e. less than about 400 molar parts of water per million parts of methyl chloride) by carrying out a distillation of the wet methyl chloride in the presence of at least ten (10) molar percent hydrogen chloride based on the methyl chloride, water and any other components of the mixture to be distilled. The distillation is carried out under super atmospheric pressure and a temperature to produce an aqueous hydrochloric acid of less than 36 wt %, and preferably under such super atmospheric pressure and sufficient temperature to produce an azeotropic hydrochloric acid containing a low concentration of hydrogen chloride. Increasing pressures allows increasing temperatures in the bottoms which form azeotropes of lower concentration hydrochloric acid.

The variables which may be adjusted to provide a lower water content of the methyl chloride and/or a higher or lower acid concentration are the molar percent hydrogen chloride, the reflux ratio, the number of trays (theoretical), the pressure and/or temperature. These variables are compensatory of each other within the general principles of distillation.

The process of the present invention is useful to dry methyl chloride whether the wetness be from a physical contacting or chemical reaction resulting in the co-mingling of the methyl chloride with water. For example, methyl chloride produced by the hydrochlorination of methanol is as readily dried as methyl chloride physically mixed with water as a result of a treatment of a material in the presence of water and methyl chloride.

The process is preferably carried out under superatmospheric pressure from about 100 psig to about 300 psig. Employing temperatures at which the azeotrope of aqueous hydrochloric acid boils for such pressure are preferable, although lower temperatures are useful if a high acid concentration is desired. Reflux ratios of between about 1.3 and 4.0 are desirable to obtain efficient use of the hydrogen chloride. Conveniently, the theroretical number of plates in the rectifier or column can vary from about 10 to about 150.

The introduction of hydrogen chloride into the system to obtain the desired distillation conditions is generally made at the still but may be present in the feed as a result of employing an excess over stoichiometric proportions in a reaction, for example in which methyl chloride is produced, or present as a by-product of a process.

DETAILED DESCRIPTION OF THE INVENTION

EXAMPLE 1

Methanol (2.903 lb. mole) was reacted with 39.7% molar excess above stoichiometric of hydrogen chloride at 166° C. The resulting effluent, methyl chloride, water and unreacted hydrogen chloride, was fed to a 5½ inch I.D. × 50 ft. high distillation column packed with ½ inch "Intalox" saddles. The still was operated at 250 psig, 210° C. reboiler with a reflux condenser at 64° C. The molar reflux was set at 2.04. The gaseous product was analyzed for water and found to contain less than 200 ppm water. The still bottoms was 9.95% aqueous hydrochloric acid.

EXAMPLE 2

The following table reports the results obtained by distilling a feed mixture of methyl chloride, water and hydrogen chloride under the indicated conditions in a similar still as described in Example 1 under the pressure conditions set forth. The amount of hydrogen chloride indicated in the table is based on the hydrogen chloride, methyl chloride and water in the feed to the distillation section. Most runs were made without measuring the reboiler liquid temperature, thus, the temperature was not controlled to produce the azeotropic boiling point temperature at the indicated pressure. The temperature of the reboiler was below the azeotropic boiling point yielding a higher acid content than would be obtained if the azeotrope boiling point had been achieved.

| Feed to Still | | | Overhead | | | Bottoms | Still | |
|---|---|---|---|---|---|---|---|---|
| HCl Mole % | MeCl Mole % | H₂O Mole % | MeCl Mole % | HCl Mole % | H₂O Mole ppm. | Aqueous HCl Wt. % | Reflux Ratio | Pressure Psig. |
| 21.5 | 39.2 | 39.2 | 68.0 | 32.0 | 200 | 13.19 | 1.83 | 252 |
| 21.1 | 39.4 | 39.4 | 68.0 | 32.0 | 180 | 11.51 | 1.79 | 254 |
| 21.2 | 39.4 | 39.4 | 67.9 | 32.1 | 160 | 11.59 | 1.79 | 254 |
| 16.6 | 41.7 | 41.7 | 75.0 | 25.0 | 210 | 11.46 | 2.14 | 251 |
| 16.6 | 41.7 | 41.7 | 75.0 | 25.0 | 220 | 11.52 | 2.09 | 251 |
| 13.6 | 43.2 | 43.2 | 80.0 | 20.0 | 190 | 12.02 | 2.06 | 249 |
| 14.3 | 42.8 | 42.8 | 78.9 | 21.1 | 170 | 11.70 | 1.99 | 249 |
| 20.6 | 39.7 | 39.7 | 69.3 | 30.7 | 210 | 14.92 | 2.29 | 120 |
| 20.3 | 39.9 | 39.9 | 69.3 | 30.7 | 230 | 14.42 | 2.34 | 120 |
| 20.4 | 39.8 | 39.8 | 69.7 | 30.3 | 220 | 13.96 | 1.36 | 150 |
| 19.7 | 40.1 | 40.1 | 71.6 | 28.4 | 390 | 16.37 | 1.48 | 150 |
| 19.6 | 40.2 | 40.2 | 75.0 | 25.0 | 118 | 24.5 | 3.58 | 120 |
| 19.7 | 40.2 | 40.2 | 75.0 | 25.0 | 122 | 25.1 | 3.62 | 120 |

We claim:

1. A method for drying water-wet methyl chloride which comprises distilling the water-wet methyl chloride in the presence of at least 10 molar % hydrogen chloride based on the total weight of acid, water and methyl chloride, as the sole dehydrating agent, under a superatmospheric pressure and a reflux ratio of from about 1.3 to about 4 and a temperature of from about 100° C. to about the azeotrope boiling point under the pressure of said distillation thereby to produce a bottoms from said distillation of not more than about 36% aqueous hydrochloric acid and an overhead of methyl chloride and hydrogen chloride containing less than about 400 molar ppm water.

2. The method of claim 1 wherein said molar quantity of HCl is at least 15% and the reflux ratio is at least 2.0.

3. The method of claim 1 wherein said molar quantity of HCl is at least 12% and the reflux ratio is at least 1.99.

4. The method of claim 1 wherein said molar quantity of HCl is at least 19% and the reflux ratio is at least 1.79.

5. The method of claim 1 wherein said molar quantity of HCl is at least 20% and the reflux ratio is at least 1.36.

6. A method for reducing the water content of methyl chloride wet with water which comprises distilling the methyl chloride, as the sole dehydrating agent, and its attendant water in the presence of at least 10 molar percent hydrogen chloride under a pressure and a reflux ratio to produce a bottoms of not more than 36 percent aqueous hydrochloric acid, thereby removing overhead a methyl chloride containing less than about 400 molar ppm of water.

* * * * *

UNITED STATES PATENT AND TRADEMARK OFFICE
CERTIFICATE OF CORRECTION

PATENT NO. : 4,145,260
DATED : March 20, 1979
INVENTOR(S) : Steele et al

It is certified that error appears in the above–identified patent and that said Letters Patent are hereby corrected as shown below:

Col. 2, line 12; change "theroretical" to --theoretical--.

Col. 3, line 4; insert --, as the sole dehydrating agent,-- between "chloride" and "based".

Col. 3, line 5; delete ", as the sole dehydrating agent,".

*Signed and Sealed this*

*Twenty-fourth* Day of *July 1979*

[SEAL]

*Attest:*

*Attesting Officer*

LUTRELLE F. PARKER
*Acting Commissioner of Patents and Trademarks*

UNITED STATES PATENT AND TRADEMARK OFFICE
CERTIFICATE OF CORRECTION

PATENT NO. : 4,145,260

DATED : March 20, 1979

INVENTOR(S) : John M. Steele, et al

It is certified that error appears in the above-identified patent and that said Letters Patent are hereby corrected as shown below:

Column 4, line 9; delete ",as the sole dehydrating agent,"

Column 4, line 11; insert --,as the sole dehydrating agent,-- between "chloride" and "under".

Signed and Sealed this

Twenty-fifth Day of November 1980

[SEAL]

Attest:

SIDNEY A. DIAMOND

Attesting Officer

Commissioner of Patents and Trademarks